United States Patent [19]

Söderberg

[11] Patent Number: 4,772,204
[45] Date of Patent: Sep. 20, 1988

[54] IMPLANT FOR ATTACHMENT OF DENTAL PROSTHESES

[75] Inventor: Per O. Söderberg, Stockholm, Sweden

[73] Assignee: Astra Meditec Aktiebolag, Sweden

[21] Appl. No.: 763,139

[22] PCT Filed: Nov. 23, 1984

[86] PCT No.: PCT/SE84/00403
§ 371 Date: Jul. 22, 1985
§ 102(e) Date: Jul. 22, 1985

[87] PCT Pub. No.: WO85/02337
PCT Pub. Date: Jun. 6, 1985

[30] Foreign Application Priority Data

Nov. 25, 1983 [SE] Sweden ............................ 8306535

[51] Int. Cl.⁴ .............................................. A61C 8/00
[52] U.S. Cl. ................................................. 433/174
[58] Field of Search ............... 433/173, 174, 176, 175

[56] References Cited

U.S. PATENT DOCUMENTS 4,177,562 12/1979 Miller et al. ......................... 433/174
4,187,609 2/1980 Ebelman ............................. 433/176
4,416,629 11/1983 Mozsary et al. .................... 433/173

FOREIGN PATENT DOCUMENTS 926552 5/1973 Canada ............................... 433/173
WO83/00616 4/1983 PCT Int'l Appl. .
332486 2/1971 Sweden .

OTHER PUBLICATIONS

P-I Branemark et al., "Osseointegrated Implants in the Treatment of Edentulous Jaw", 1977, pp. 21–38.
Proceedings of the Toronto Conference on Osseointegration in Clinical Dentistry, reprinted from The Journal of Prosthetic Dentistry, vol. 49, No. 6 (Jun., 1983), and vol. 50, Nos. 1, 2 and 3 (Jul., Aug. and Sep., 1983).

Primary Examiner—Robert Peshock
Attorney, Agent, or Firm—Brumbaugh, Graves, Donohue & Raymond

[57] ABSTRACT

Implant intended to facilitate attachment of dental prostheses against a jaw-bone (2), including an externally threaded screw-shaped member (1), intended to be attached against a threaded hole taken up in the jaw-bone (2). In difference to previously known types of implants, the screw-shaped member (1) includes a blind hole directed from the jaw-bone (2), the first portion of which is a conically tapering portion (4), which is transformed into an internally threaded hole (3). Since the conical portion (4) adjacent to the end surface of the screw-shaped member (1) preferably is arranged with a diameter smaller than the outside diameter of the end portion, and since a cover screw with a conical head which is substantially enclosed by the conical portion (4) is utilized during the osseointegration process, the jaw-bone (2) can be permitted to enclose and encapsulate this end portion of the screw-shaped member (1) during the osseointegration process. A pillar (6) can be attached against the screw-shaped member (1), at an opposed end portion supporting a conical tubular member (7), arranged to facilitate a resilient movement in relation to the pillar (6), whereby a dental prosthesis can be attached having a restricted movement in relation to the jaw-bone (2).

10 Claims, 1 Drawing Sheet

# IMPLANT FOR ATTACHMENT OF DENTAL PROSTHESES

CROSS REFERENCE TO RELATED APPLICATION(S)

This U.S. application stems from PCT International Application No. PCT/SE84/00403 filed Nov. 23, 1984.

The present invention relates to an implant for attachment of dental prostheses.

An implant is an anchoring means, which is specifically intended to facilitate anchoring of dental prostheses in the jaw-bone, and which is used when other possibilities of attachment do not exist.

Previously known anchoring means, hereinafter referred to as implants, comprise an externally threaded screw-shaped member which is arranged with an upper portion shaped as a cylindrical screw head, having the top portion arranged as an hexagonal attachment portion which is intended to facilitate attachment with an associated tool. A blind hole extends from said attachment portion, arranged with an internal screw thread.

When such implants are used, a small incision is made in the buccal mucoperiosteum, thereby revealing the jaw-bone. Thereafter a hole is drilled in the jaw-bone, first with a dental drill and then with a larger special purpose drill, whereafter the hole is threaded with a screw tap. After cleaning the hole, the screw-shaped member is screwed down into the hole with use of a special purpose tool which attaches to the hexagonal attachment portion. A cover screw is thereafter attached to the internally threaded hole in the screw-shaped member. Said cover screw includes a screw head which covers the attachment portion existing at the screw-shaped member. The gum is thereafter sewn together over the attached device, which is left during a period of 4-6 months to osseointegrate with the jaw-bone.

After this period of time, the device is revealed, and the cover screw removed. A pillar, having a first portion with cylindrical cross-section extending from an end surface, which is followed by a second portion with a smaller diameter and having an external screw thread, is screwed with the threaded portion into the internally threaded hole within the screw shaped member attached to the jaw-bone. From the end surface wherefrom the first cylindrical portion extends, a centrally located blind hole extends into the pillar, arranged with an internal screw thread. A matrix pillar is attached to said threaded hole, arranged substantially corresponding to the previously discussed pillar, apart from the internally threaded hole. A proof impression is made thereafter, intended to be utilized by a dental technician when manufacturing the bridge. The matrix pillar and the pillar are then removed and the cover screw reattached. The buccal mucoperiosteum is returned back over the members attached to the jaw-bone, pending the completion of the work on the bridge by the dental technician.

When manufacturing the bridge, every impression of a matrix pillar is used to accomplish a through hole in the supporting metal structure located behind the teeth front. When attaching the bridge, the cover screw is removed and replaced by the previously utilized pillar. An attachment screw is applied against the bridge and attached with its threaded portion against the internally threaded hole in the pillar, whereafter the hole in the metal structure of the bridge, above the head of the attachment screw, is filled with a suitable material, e.g. a synthetic resin material.

Certain modifications with regard to the above described previously known implant are also known, and particularly with regard to the design of the pillar. Previously used pillars have been designed to include a tubular cylindrical member in combination with a screw-shaped member which, in accordance with the member attachable to the jaw-bone, is arranged with a head having a hexagonal attachment member. Said attachment member is, when mounted, embraced by a tubular distance means arranged in an intermediate position between the upper end surface of the cylindrical member and the bridge intended to be attached. The number of implants used is related to the extension of the bridge, but for attachment of a complete bridge, a number of six implants can usually be regarded as sufficient.

However, the above described and previously known implant has a number of disadvantages, and as a result, these implants can only be used by specially trained dentists. Moreover, the cost for each attached implant has also been relatively high. The implants are usually manufactured from titanium, and all the special tools utilized during the operation of attachment are therefore also manufactured from the same material. A normally occurring problem is to accomplish complete matching between the implants attached to the jaw-bone and the metal structure of the bridge. When the bridge is attached, side directed forces often occur in relation to the members attached to the jaw-bone. The method in which included members abut each other with adjacently located side surfaces also result in sealing problems, and the design results in a rigid attachment, different from natural teeth, which can perform a small movement in relation to the jaw-bone.

The object of the present invention is to disclose an improved implant, which eliminates the disadvantages of previously known types, and which includes a small number of parts which can be supplied and attached to a considerably reduced cost. Heretofore described problems with regard to sealing and adjustment to the bridge are also substantially diminished. The present invention also offers possibility of accomplishing attachment of the bridge in relation to the jaw-bone in a fashion which substantially corresponds to the attachment of natural teeth, i.e. with a restricted movement in relation to the jaw-bone.

An embodiment of an implant according to the present invention, and certain modifications thereof, are more fully described below with reference to the accompanying drawings, in which.

Figure 1:
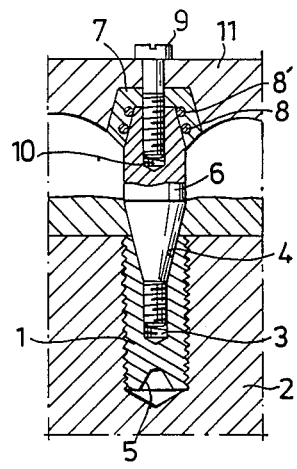
FIG. 1 shows a cross-sectional view of an implant according to the present invention, arranged in attachment to a jaw-bone and supporting a bridge.

With reference to FIG. 1, the implant according to the present invention includes, as in previously known types of implants, an externally threaded screw-shaped member, intended to be attached against a threaded hole taken up in a jaw-bone 2. As opposed to previously known types, the screw-shaped member 1 includes not only an internally threaded blind hole 3, but also an internal conical portion 4, arranged by the first portion of the blind hole which is taken up in the screw-shaped member 1. The screw-shaped member 1 is arranged substantially cylindrical, having at least one cross-wisely extending groove 5 at the end portion which serves as a first end portion during the attachment of the screw-shaped member 1 against the jaw-bone 2. At the opposite end portion, the conical portion 4 is arranged with a smaller diameter than the outside diameter of said end portion.

A pillar 6 is attached against the screw-shaped member 1, including a threaded portion directed towards the screw-shaped member 1, which is followed by a conical portion having a conicity corresponding to the internal conical portion 4. The conical portion of the pillar 6 is preferably arranged having a longer extension, and is followed by a cylindrical portion, which is terminated by a second conical portion against which a tubular member 7 abuts, arranged with an internal conical portion. Adjacent to the internal conical surface of the tubular member 7, two spaced grooves are taken up, in which two O-rings 8, 8' are arranged. The outside surface of the tubular member is also arranged as a conical surface, and on the end surface directed away from the pillar 6, a centrally located through hole is taken up, through which an attachment screw 9 extends, attached against an internally threaded hole 10 taken up in the pillar 6. The head of the attachment screw 9 abuts a supporting metal structure 11, which comprises a part of the bridge intended to be attached.

Figure 2:
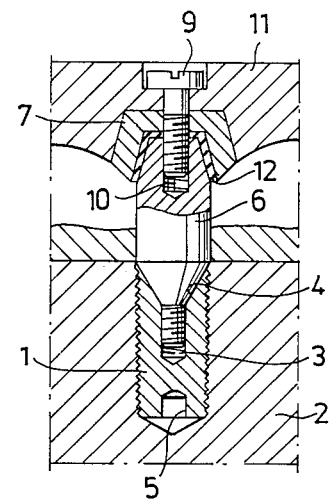
FIG. 2 shows a cross-sectional view corresponding to FIG. 1, with the implant slightly modified.

A slightly modified embodiment is shown in FIG. 2, which only differs from the embodiment shown in FIG. 1 with regard to two aspects. Accordingly, the previously mentioned O-rings, 8, 8' have been replaced by a layer 12 intermediate in relation to the pillar 6 and the tubular member 7. Layer 12 is comprised of a compressible material, such as rubber, synthetic rubber, synthetic plastic or the like. Furthermore, the internal conical portion 4 has been arranged extending to the upper edge portion of the screw-shaped member 1, and the cylindrical portion of the pillar 6 is arranged extending to the upper edge portion of the screw-shaped member 1. The intermediately located layer 12 can either be joined with the conical surface of the conical member 7, or alternatively comprise a coating joined with the co-acting conical surface of the pillar 6. The layer 12 can also comprise a conical collar-shaped member, which is placed between the conical surfaces of the pillar 6 and the tubular member 7.

Figure 3:
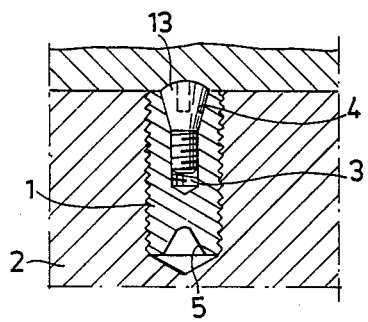
FIG. 3 shows a cross-sectional view of the implant attached to a jaw-bone during a first stage of the attachment.

When the present invention is used, an incission is made in the buccal mucoperiosteum, thereby revealing the jaw-bone 2. Thereafter a hole is taken up and threaded so as to facilitate attachment of the screw-shaped member 1. An attachment tool can be a longitudinally extending member, having one end portion arranged to suit the upper portion of the screw-shaped member 1, i.e. with a threaded portion facilitating attachment against the internally threaded hole 3. When the screw-shaped member 1 has been screwed down into the threaded hole taken up in the jaw-bone 2, the attachment tool is removed, and a cover screw 13 is attached. Said cover screw is arranged with a conical head, the outside surface of which is located adjacent to the upper portion of the screw-shaped member 1. Thereafter the buccal mucoperiosteum is moved back over the cover screw 13, and the screw-shaped member 1 is left for a certain period of time, e.g. 4 months, to osseointegrate with the jaw-bone 2. This first stage of the attachment operation is shown more in detail in FIG. 3.

By utilizing the embodiment of FIG. 1, an extremely advantageous effect is accomplished during the osseointegration procedure-encapsulating the attached screw-shaped member 1. Since the jaw-bone can grow over the outer and upper edge portions of the screw-shaped member 1, this results in improved anchoring properties and also substantially removes the risk for penetration of impurities and bacteria cultures down between the screw-shaped member 1 and the threaded hole taken up in the jaw-bone 2. The method in which the cover screw 13 substantially is enclosed by the screw-shaped member 1 is a further advantage in relation to previously known designs, partly due to the improved sealing accomplished by the conical end against each other abuting surface and partly due to the fact that the gum is not unneccesarily irritated by a screw head located above the screw-shaped member 1.

Figure 4:
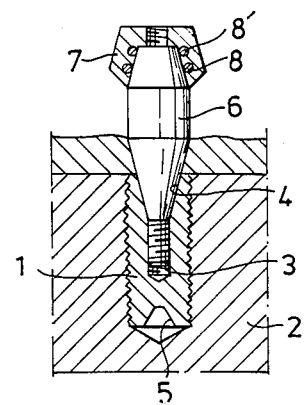
FIG. 4 shows a cross-sectional view of the implant during a second stage of the attachment.

When the necessary period of time for osseointegration has passed, the buccal mucoperiosteum is opened again and the cover screw 13 is removed and replaced by a pillar 6, on which an associated tubular member 7 is located. Thereafter, a proof impression is made, and the tubular member 7 is permitted to follow the impression when same is removed. The pillar 6 is thereafter removed and replaced by cover screw 13, whereafter the buccal mocoperiosteum is moved back over the attached implant while waiting for the dental technicians to complete their work with the bridge construction intended to be attached. The method in which included members are located during the proof impression operation is shown in FIG. 4. It should be mentioned that, when manufacturing the bridge, the tubular member 7 is not attached against the supporting metal structure 11, but only holes for same are taken up.

When the dental technicians work has been completed, matching and attachment can be performed. The cover screws 13 utilized is revealed and removed, and replaced by pillar 6. Conical tubular member 7 is thereafter located on said pillar and matching in relation to the metal structure of the bridge 11 is checked. During subsequent matching check, when required, necessary adjustments with regard to the holes taken up in the metal structure of the bridge is performed for the tubular member 7. When complete matching has been accomplished, the conical tubular member 7 is cemented to the metal structure 11, whereafter same is lifted off the pillar 6. Provided that the artificial teeth have not already been attached, the metal structure 11 is now returned to the dental technician before final attachment is performed, which is performed by attachment of attachment screw 9 in the holes taken up in the metal structure 11, which are screwed into the threaded hole 10 taken up in the pillar 6. By utilizing O-rings 8, 8', or an intermediately located layer 12, the attached prosthesis receives a certain resilient movement in relation to the jaw-bone, and said resilient movement is comparable to the movement of natural teeth. This effect is particularly advantageous when attaching smaller bridges for a person having natural teeth. The teeth of the bridge will thus achieve a pattern of movement which substantially corresponds with the natural teeth, which must be regarded as a considerable improvement in relation to previous dental prostheses ridgidly attached against the jaw-bone.

The implant according to the present invention thus offers a number of advantages in relation to previously known techniques, due to the fact that the invention includes a smaller number of parts, and thus has a reduced manufacturing cost, due to the improvement disclosed above with relation to osseointegration properties, simplified and improved matching, and also because of the possibility of resilient attachment now offered. Similar to previously known types of implants, the implant according to the present invention is preferably manufactured from titanium, a material which has been proved suitable for this purpose, but other materials can also be used. As a possible and suitable modification, the conical tubular member 7 can be manufactured from another material, such as a synthetic plastic material with compressible properties, which material would not require O-rings 8, 8', or a layer 12, in order to accomplish desired resilient attachment.

Other smaller modifications can obviously be made, such as with regard to the method in which attachment is accomplished between utilized tools and the members included in the implant, which obviously can be arranged with attachment means of other types than shown and described.

It is also possible to arrange the conical portion of the pillar 6 directed away from the screw-shaped member 1 with one or a number of grooves in the conical surface, extending in longitudinal direction of the pillar 6. This would offer the possibility of attaching single teeth with the implant, and to accomplish security against rotation of same from a predetermined position when used. The tubular member 7 can in this case advantageously serve as the supporting metal structure for such a single tooth, and be accomplished by a proof impression operation, whereby its internal conical surface receives outwardly extending portions which can grip into the grooves taken up in the pillar 6. Furthermore, when a slightly resilient attachment is desired for such single teeth, the previously mentioned intermediately located layers 12 may be used.

I claim:

1. A dental implant for anchoring a dental prosthesis to a jaw-bone of a patient in need of such prosthesis, said dental implant comprising an outwardly threaded cylindrical screw member for attachment and osseointegration in a cylindrical bore in said jaw bone, said screw member having an axial blind hole having a first conical portion tapering substantially from one end of said screw member through a portion of the length of said screw member, and continuing into an inwardly threaded cylindrical portion, said hole being adapted to receive and substantially embrace during a first osseointegration stage a cover screw having complementary conical and outwardly threaded cylindrical portions; said dental implant further comprising a prosthesis-supporting pillar adapted to be received and firmly attached in said hole, said pillar having a first conical portion and an outwarly threaded cylindrical portion complementary to the corresponding portions of the hole, and a second conical portion tapering to the opposite end of said pillar; the dental implant further comprising a conical tubular member adapted to fit over said second conical portion and to fit into a complementary hole in a dental prosthesis.

2. An implant according to claim 1, wherein in that the conical hole-shaped portion adjacent to the end surface of the screw-shaped member has a smaller diameter than the diameter of said end surface.

3. An implant according to claim 1, wherein in that the cover screw, which during a first stage is used attached to the screw-shaped member, is arranged with a conical screw head having a shape and extension substantially corresponding to the conical hole-shaped portion in the screw-shaped member.

4. An implant according to claim 1, wherein in that the pillar includes a centrally and substantially cylindrical portion, which at first end portion is transformed into a conically tapering portion having a configuration and extension substantially corresponding to the conical hole-shaped portion in the screw-shaped member, and with an externally threaded portion extending therefrom, attachable against the internally threaded blind hole, and that the second end portion is arranged as a conically tapering part, including a centrally located internally threaded blind hole.

5. An implant according to claim 1, wherein in that the tubular member is arranged with both a conical outside and inside surface.

6. An implant according to claim 1, wherein in that in an intermediate position in relation to the pillar and the tubular member are arranged one or a number of resilient compressable means, arranged to facilitate a restricted movement of the tubular member in relation to the pillar.

7. An implant according to claim 1, wherein in that intermediately located between the pillar and the tubular member is arranged a layer or a coating of resilient compressable material, arranged to facilitate a restricted movement of the tubular member in relation to the pillar.

8. An implant according to claim 1, wherein in that the tubular member is manufactured from a resilient compressable material, such as synthetic plastic or similar.

9. An implant according to claim 1, wherein in that the tubular member is attached against the supporting metal structure of the dental prosthesis by means of cementation, glueing or similar, when the prosthesis is tried out for matching.

10. An implant according to claim 1, wherein in that a conical portion of the pillar directed away from the screw-shaped member includes at least one groove taken up in the surface, extending in longitudinal direction of the pillar, arranged in a number corresponding to outwardly extending portions at the internal conical surface intended to be attached in an adjacent position to the conical portion of the pillar.

* * * * *